(12) United States Patent
Muccio (10) Patent No.: US 11,679,251 B2
(45) Date of Patent: Jun. 20, 2023

(54) LOWER BACK ELECTRICAL STIMULATOR

(71) Applicant: Philip Muccio, Ypsilanti, MI (US)

(72) Inventor: Philip Muccio, Ypsilanti, MI (US)

( * ) Notice: Subject to any disclaimer, the term of this patent is extended or adjusted under 35 U.S.C. 154(b) by 0 days.

(21) Appl. No.: 15/311,626

(22) PCT Filed: May 15, 2015

(86) PCT No.: PCT/US2015/031183
§ 371 (c)(1),
(2) Date: Nov. 16, 2016

(87) PCT Pub. No.: WO2015/175996
PCT Pub. Date: Nov. 19, 2015

(65) Prior Publication Data
US 2017/0072185 A1    Mar. 16, 2017

Related U.S. Application Data

(60) Provisional application No. 61/994,441, filed on May 16, 2014.

(51) Int. Cl.
*A61N 1/04* (2006.01)
*A61N 1/36* (2006.01)

(52) U.S. Cl.
CPC ........... *A61N 1/0452* (2013.01); *A61N 1/048* (2013.01); *A61N 1/0484* (2013.01); *A61N 1/0492* (2013.01); *A61N 1/36003* (2013.01); *A61N 1/36021* (2013.01)

(58) Field of Classification Search
CPC ................ A61N 1/0452; A61N 1/0484; A61N 1/36003; A61N 1/36021
See application file for complete search history.

(56) References Cited

U.S. PATENT DOCUMENTS

| 4,381,012 A * | 4/1983 | Russek ................ A61N 1/0484 600/382 |
| 7,899,556 B2 * | 3/2011 | Nathan .............. A61N 1/36003 607/144 |
| 2002/0032475 A1 * | 3/2002 | Arbel ................... A61N 1/0456 607/149 |
| 2002/0058972 A1 * | 5/2002 | Minogue ................ A61N 1/321 607/72 |
| 2003/0114893 A1 * | 6/2003 | Nathan ................ A61N 1/0476 223/111 |
| 2010/0130847 A1 * | 5/2010 | Dunagan .............. A61B 5/0408 600/389 |
| 2011/0093035 A1 * | 4/2011 | Moser ................ A61N 1/36003 607/48 |

(Continued)

FOREIGN PATENT DOCUMENTS

WO    WO 2010/027874    *    3/2010    ............... A61N 1/36

*Primary Examiner* — Eric D. Bertram
(74) *Attorney, Agent, or Firm* — Mindful IP PLLC; Michael J. McCandlish (57) ABSTRACT

The electrical stimulation belt includes an electrical stimulator, a flexible substrate, a plurality of electrical connectors, a plurality of electrodes and a plurality of locators. The electrical stimulation is applied to the trunk or waist of a patient by the electrical stimulator belt through the placement of the plurality of electrical connectors in contact with the plurality of electrodes on the belt. A plurality of locators releasably fastened to the belt assist the user in locating the electrodes on the belt.

14 Claims, 5 Drawing Sheets

(56) References Cited

U.S. PATENT DOCUMENTS

| | | | |
|---|---|---|---|
| 2012/0203156 A1* | 8/2012 | Dar | A61F 5/0106 602/5 |
| 2012/0330394 A1* | 12/2012 | Dar | A61F 5/0102 607/149 |
| 2013/0110220 A1* | 5/2013 | Brown | A61N 1/0452 607/149 |

* cited by examiner

LOWER BACK ELECTRICAL STIMULATOR

RELATED APPLICATIONS

This application claims the benefit of International Application PCT/US15/31183 filed May 15, 2016 which claims benefit of U.S. Provisional Patent Application No. 61/994,441, filed on May 16, 2014. The entire contents of the above cited application are incorporated herein by reference.

FIELD

The present invention relates to electrical stimulation devices and, in particular, wearable electrical stimulation devices configured to be worn on the lower back.

BACKGROUND

Electrical stimulation of muscles and nerves has been employed over the years to treat certain medical conditions. Typically an electrical stimulation device has a plurality of electrodes attached to a substrate that is configured to be worn by a patient. One difficulty is to properly and accurately locate the electrodes along the patient's body part to be treated.

Accordingly, there is room in the art for an electrical stimulation device that is configured to accurately locate the electrodes on the portion of the body part to be treated. Moreover, there is need for an electrical stimulation device or garment that incorporates electrodes that are easily removed from the garment and reattached at the proper location.

SUMMARY

In an aspect of the present invention, an electrical stimulation belt is provided. The electrical stimulation belt includes an electrical stimulator, a flexible substrate having two side panels and a back panel, a plurality of electrical connectors, a plurality of electrodes and a plurality of locators.

In accordance with an embodiment of the present invention, the electrical stimulator is configured to generate an electrical current sufficient to cause muscle contraction in a body part.

In accordance with another embodiment of the present invention, the flexible substrate is made of a Neoprene material.

In accordance with yet another embodiment of the present invention, the plurality of electrical connectors are in electrical communication with the electrical stimulator and releaseably attached to the back panel.

In accordance with yet another embodiment of the present invention, the plurality of electrodes are releaseably connected to the plurality of electrical connectors.

In accordance with yet another embodiment of the present invention, the plurality of locators are releaseably connected to the back panel to indicate the placement of the plurality of electrical connectors or domatrodes.

In accordance with yet another embodiment of the present invention, electrical stimulation is applied to the body part by the electrical stimulator through the placement of the plurality of electrical connectors in contact with the plurality of electrodes to a prescribed area of the trunk or waist as identified by the plurality of locators.

In accordance with still another embodiment of the present invention, the plurality of electrical connectors each includes a magnet.

In accordance with still another embodiment of the present invention, the plurality of electrodes each includes a magnet.

In accordance with still another embodiment of the present invention, the plurality of electrical connectors each includes a layer of velcro for releaseably attaching each of the plurality of electrical connectors to the back panel.

In accordance with still another embodiment of the present invention, the plurality of electrodes each includes a layer of velcro for releaseably attaching each of the plurality of electrodes to the back panel.

In accordance with still another embodiment of the present invention, the electrical stimulation belt further includes a plurality of lead wires for electrically interconnecting the plurality of electrical connectors or domatrodes with the electrical stimulator.

In accordance with still another embodiment of the present invention, the plurality of locators each includes a layer of Velcro for releaseably attaching each of the plurality of locators to the substrate to indicate the preferred placement of the plurality of electrical connectors or domatrodes.

Further features, advantages and areas of applicability will become apparent from the description provided herein. It should be understood that the description and specific examples are intended for purposes of illustration only and are not intended to limit the scope of the present disclosure.

DRAWINGS

The drawing described herein is for illustration purposes only and is not intended to limit the scope of the present disclosure in any way. In the drawing.

DETAILED DESCRIPTION

The following description is merely exemplary in nature and is not intended to limit the present disclosure, application, or uses.

Figure 1:
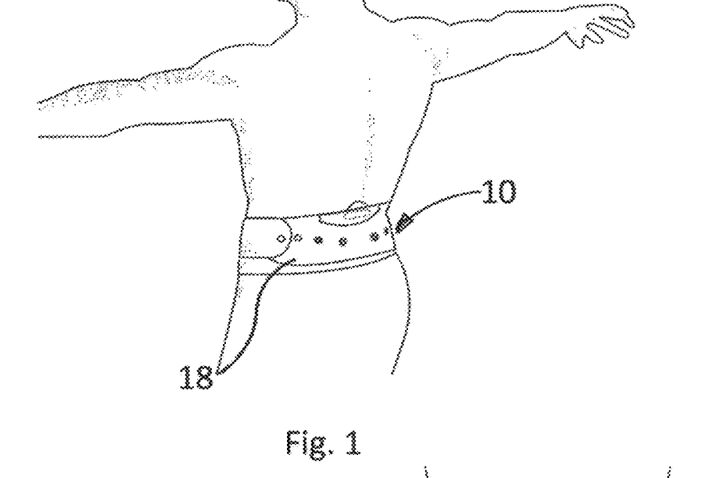
FIG. 1 is a rear perspective view of an electrical stimulation garment worn on the lower back to stimulate nerves and muscles, in accordance with the principles of the present invention.
Figure 2:
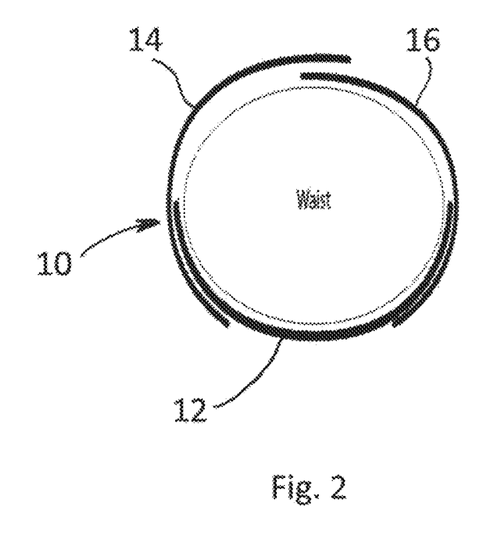
FIG. 2 is a top perspective view of the electrical stimulation garment worn on the lower back to stimulate nerves and muscles, in accordance with the principles of the present invention.
Figure 3:
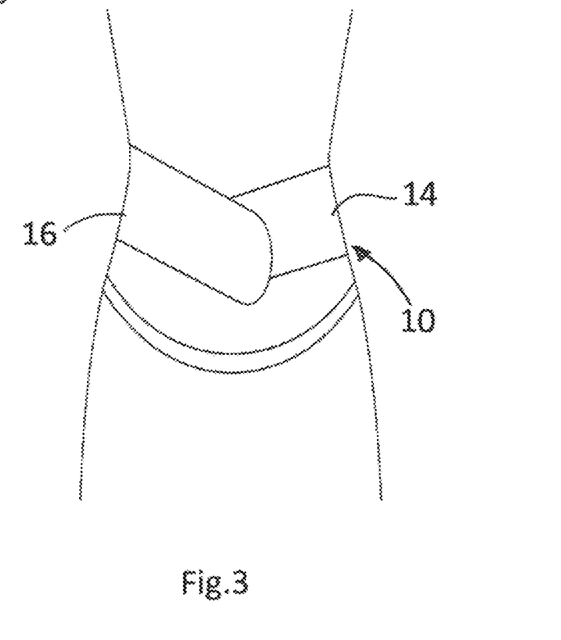
FIG. 3 is a front perspective view of the electrical stimulation garment worn on the lower back to stimulate nerves and muscles, in accordance with the principles of the present invention.

Referring now to FIGS. 1-3, perspective views of a lower back electrical stimulator belt 10 are illustrated. The stimulator belt 10 is an electrical stimulation garment worn on and around the lower back to stimulate nerves and muscles to produce various desirable medical outcomes such as relief of chronic pain, relaxation of muscle spasms, increased range of motion of lumbar spine, increased circulation to underlying muscles, to re-educate muscles, to facilitate movement of the trunk and reduce compensatory movements of the body. Stimulator 10 utilizes a conventional electrical stimulator control module 11 (shown in FIG. 8) connected to a plurality of electrodes through lead wires to transmit electrical current to the electrodes and thereby the body part to be stimulated. The belt 10 has a back panel 12 and two side panels 14, 16. When all three panels are connected, the stimulator belt 10 encircles a user's trunk at the level of the lumbar spine. The panels 12, 14 and 16 are manufactured in a variety sizes and lengths and are matched with each other to achieve operable fit for the user. The side panels 14, 16 are releasably secured to the back panel 12 by a fastening system such as Velcro or hook and loop or the like. Accordingly, the side panels may be releasably attached to the back panel at different locations to increase or decrease the belt's circumference. Thus, the size of the belt 10 is adjustable to fit the user and accommodates changes in user waist circumference that may occur from time to time. Side Panels 14, 16 are interchangeable panels that dramatically increase or decrease the circumference of the belt 10. Short side panels 14, 16 make the belt 10 shorter in circumference while long side panels 14, 16 make the belt longer. Thus, the number of users that can be fit without having to manufacture multiple sized belts increase is increased. The side panels 14, 16 shift forward or backward on the back panel 12 to increase or decrease waist circumference to improve the fit of the belt 10 on the user. Moreover, the side panels are configured to pivot on the back panel to accommodate differences in waist and hip circumference that are seen in males and females. The pivoting panels feature allows the belt to be worn by both male and female users without having to have two different belt models. The belt 10 is a belt with an interior pocket. The belt 10 is made with a fastener closure at the center front to close the belt 10 around the body and accommodate small changes in waist circumference.

In one embodiment of the present invention, the belt 10 includes of a substrate 18 made of stretchable and flexible neoprene in which other components are sewn or fastened to, including domatrodes containing a stainless steel magnetic connector, lead wires, lead wire cabling, small hook dots used as domatrode locators, electrode positioning icons, electrode numbering icons, domatrode protective covers and Fastener electrodes, as will be described hereinafter. The belt 10 is semi-rigid so that is has vertical integrity so that it doesn't compress in the vertical direction over time.

In another embodiment of the present invention, substrate 12 is a flexible, Neoprene® material (S-foam) that serves as the support structure for the belt 10. The Neoprene® material of substrate 12 has bi-directional stretch so that the substrate 12 conforms to body contours around and over the trunk, as shown in FIG. 1, FIG. 2 and FIG. 3. Substrate 12 is impervious to water and moisture and does not absorb moisture. Substrate 12 can be cut without fraying.

Figure 4:
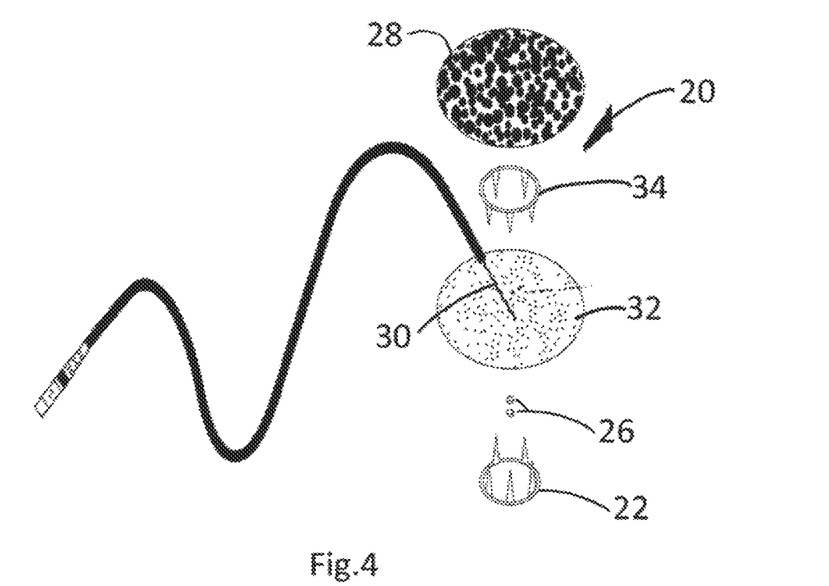
FIG. 4 is a exploded view of the electrical connector or domatrode, in accordance with the principles of the present invention.
Figure 5:
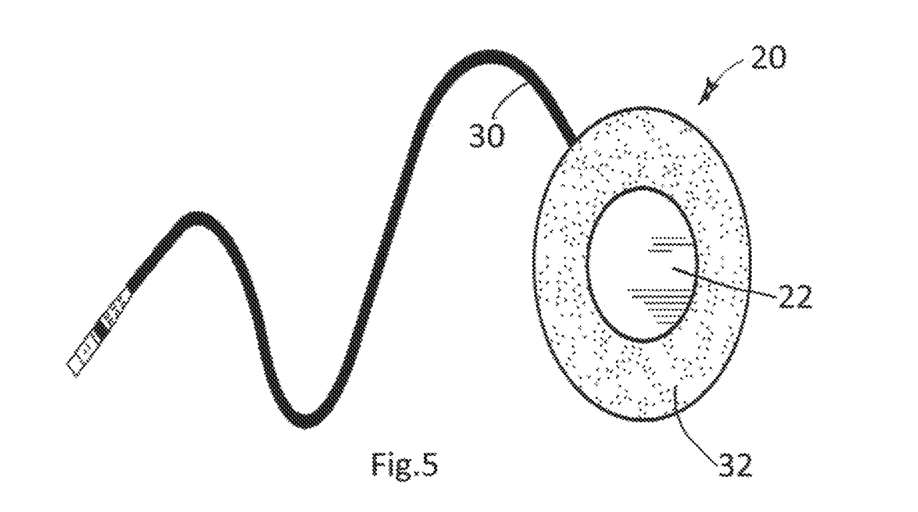
FIG. 5 is a top perspective view of the electrical connector of the electrical stimulation belt fully assembled, in accordance with the principles of the present invention.
Figure 6A:
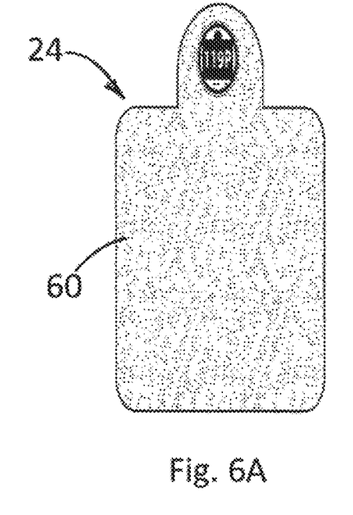
FIGS. 6A, 6B and 6C are a front view, a back side view and an exploded view of the electrode 24, in accordance with the principles of the present invention.
Figure 6B:
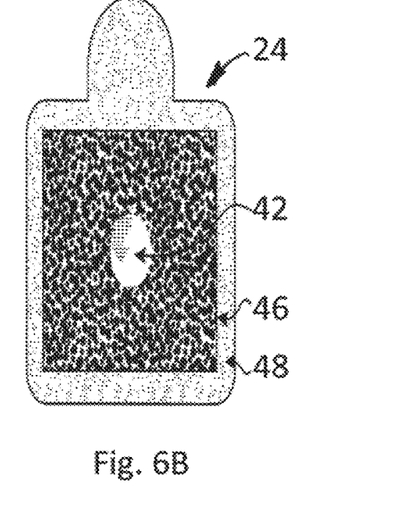
Figure 6C:
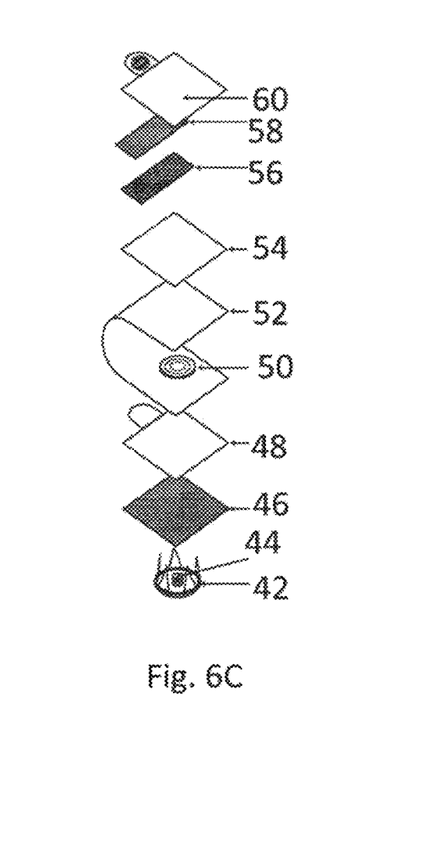

With specific reference to FIGS. 4 and 5, the domatrode 20 is an electrical connector configured to make electrical contact with a stainless steel connector or cap 22 on an electrode 24 (shown in FIG. 6A-6C). The domatrode 20 connector has a metal cap 22 that contains a low-force magnet 26. The magnet 26 inside each cap 22 provides sufficient magnetic force to cause the domatrode 20 to couple to the electrode 24, yet weak enough to allow decoupling with ease by the user by hand when removing the electrode 24 from the garment. Once the domatrode 20 is connected to the electrode 24, an electrical current can pass through the connection from the domatrode 20 to the electrode 24. The underside of the domatrode 20 has a layer hook of Velcro material 28 that mates with pile neoprene on the belt 10 which holds the domatrode 20 to the belt 10. Domatrodes 20 can be shifted to any position on the belt 10 within a certain radius to maximize the possible locations of each electrode 24. Furthermore, a lead wire 30 is sandwiched between and secured to a Darlexx Dot or circular piece 32 by the domatrode cap 22 and a domatrode socket 34. Lead wire exits through an exit hole 35 in the substrate 12 of the belt 10 and passes through the belt to connect to electrical stimulator module 11.

Referring now to FIGS. 6A 6B and 6C, a front, back and exploded views of electrode 24 are shown, in accordance with the present invention. Electrode 24 includes a metal cap 42, magnets 44, a layer of hook Velcro material 46, a layer of vinyl spandex 48, a metal socket 50, a flexible folded layer of silver paper or silver ripstop fabric 52, a layer of light spandex 54, a layer of loop Velcro material 56, a layer of hook Velcro material 58, a layer of light spandex 60. The metal cap 42 has a plurality of metal tabs that are pressed through the intermediate layers and into the metal socket 50 thereby fastening and electrically connecting the metal cap 42 to the meal socket 50. Thus, the metal cap 42, the metal socket 50 and the flexible folded layer of silver paper 52 are in electrical communication. The layer of light spandex 60 contacts the patient's skin and allows the electrical current to pass from the metal cap 42 through to the body part to be stimulated. Each electrode 24, regardless of shape or dimension, includes the metal cap 42 that mates with the metal cap 22 on the domatrode 20. The perimeter of the electrode 24 is free of Velcro material so that the user can remove the electrode 24 from the belt 10 with very little force by grab and lift the electrode 24 from the belt 10.

Figure 7A:
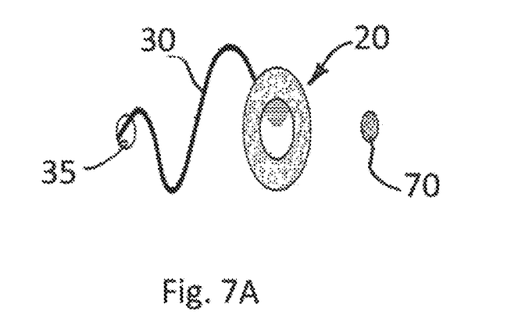
FIGS. 7A and 7B are perspective views of the electrical connector or domatrode adjacent a locator dot and over top of a locator dot, respectively, in accordance with the principles of the present invention.
Figure 7B:
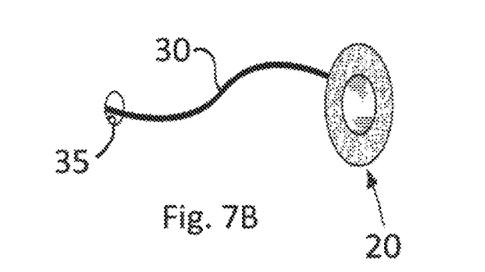

Referring now to FIGS. 7A and 7B, top views of domatrode 20 are shown releaseably attached to the substrate 12, in accordance with the present invention. Domatrodes 20 can be shifted to any position on the belt 10 within a certain radius to maximize the possible locations for an electrode 24. A Velcro locator dot 70 is a piece of material (i.e. neoprene) in the shape of a dot and has a hook Velcro fastener that fastens to the neoprene substrate 12 to mark a preferred location of the domatrode 20. Velcro locator dot 70 has a diameter smaller than the outer diameter of the domatrode 20. The Velcro locator dot 70 pin points the location of where the clinician wants to place an electrode 24 (over the domatrode 20). When the belt 10 is configured to fit a particular patient, a clinician applies the belt 10 and places a chalk mark on the outside of the belt 10 where an electrode 24 should be placed. Once the placement of the electrode 24 is determined, a Velcro dot 70 is placed on the inside of the belt exactly opposite of where the clinician marked the belt 10. The domatrode 20 is placed over the Velcro dot 70. An electrode 24 is then connected to the domatrode 20 at the location of the Velcro dot 70. The Domatrode 20 will stay fastened to the belt 10 at all times, but can be shifted to another location should the need to move an electrode 24 arise. Velcro dots 70 ensure that the location of Domatrode 20 will be maintained over time. The combination of the Velcro dots 70 and the Domatrode 20 affixed over the Velcro dots 70, ensures that the patient will place the electrode 24 in the proper location each time the belt 10 is used.

Figure 8:
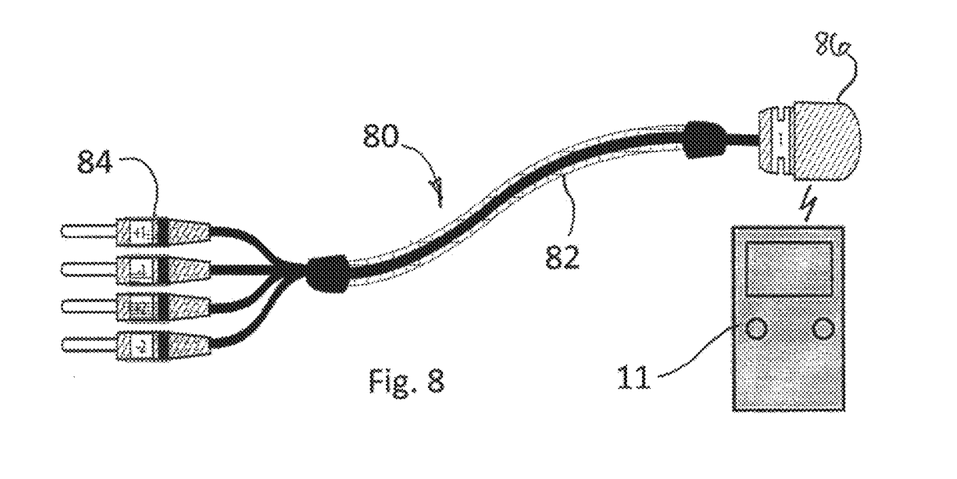
FIG. 8 is a perspective view of the lead wires of the electrical stimulation belt and the electrical stimulation module, in accordance with the principles of the present invention.
Figure 9A:
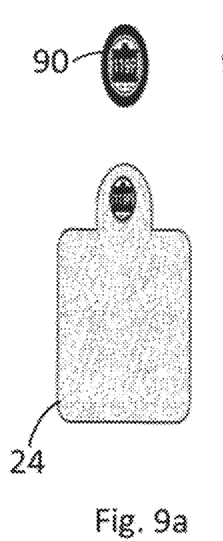
FIG. 9 is a perspective view of the electrode icons and a set of electrodes in different orientations, in accordance with the principles of the present invention.
Figure 9B:
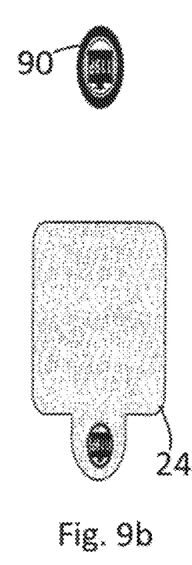
Figures 9C, 9D:
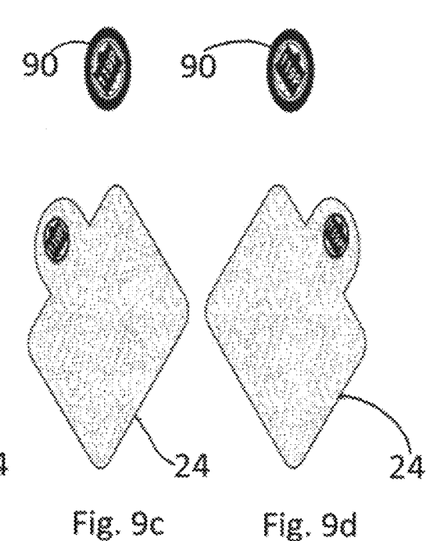

Referring now to FIG. 8, is a perspective view of lead wires 80 that are configured to connect to lead wires 30 are shown, in accordance with the present invention. Lead wires 80 are enclosed in a protective tubular weave material 82 to contain them and keep them organized. The connector end 84 of each lead wire 80 is labeled with its respective channel number so that the user is guided to insert the connector 86 into the correct receptacle on the electrical stimulator 11. This ensures that each channel of stimulation is delivered to the correct pair of electrodes. For example, channel 1 labeling is located over a first muscle group and channel 2 labeling is located over a second muscle group.

Figure 10:
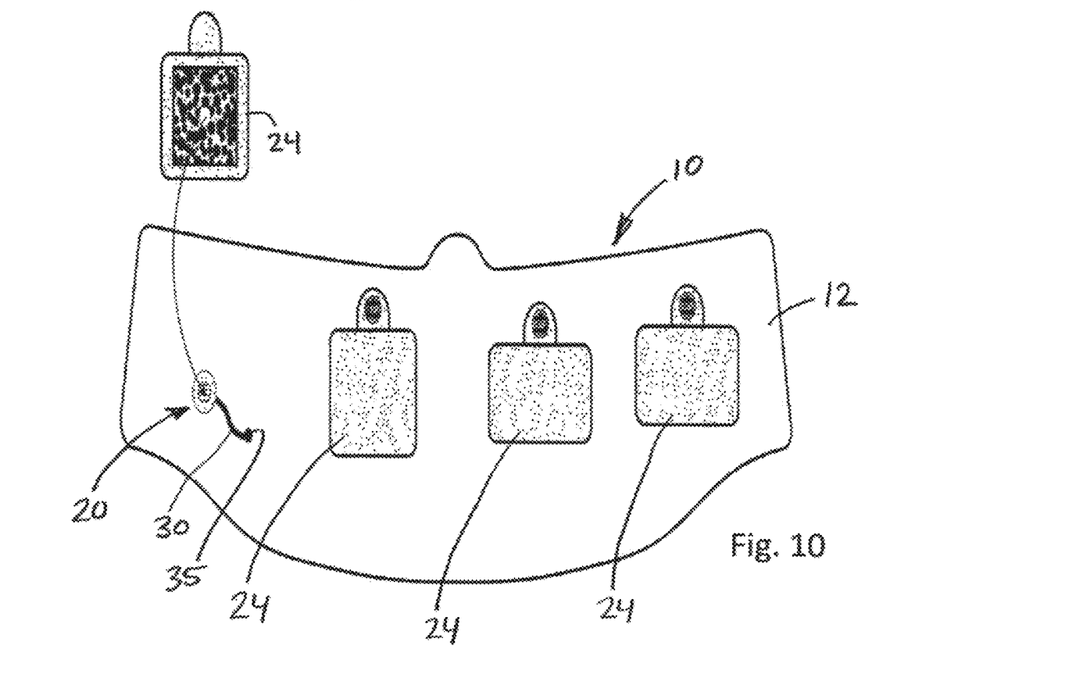
FIG. 10 is a perspective view of the electrodes releasably attached to the back panel of the belt, in accordance with the principles of the present invention.

Referring now to FIGS. 9a-9d, is a perspective view of electrode icons 90 are shown in different orientations, in accordance with the present invention. Electrode icons 90 are fastened with hook Velcro to the neoprene substrate 12 material on the inside of the belt 10. The purpose of the electrode icon 90 is to inform the user which electrode 24 is placed on the corresponding domatrode 20 and how the electrode is to be oriented on the belt 10, as illustrated in FIG. 10.

The description of the invention is merely exemplary in nature and variations that do not depart from the gist of the invention are intended to be within the scope of the invention. Such variations are not to be regarded as a departure from the spirit and scope of the invention.

What is claimed is:

1. An electrical stimulation garment comprising:
   an electrical stimulator configured to generate an electrical current sufficient to cause muscle contraction in a lower back of a patient;
   a back panel and a first and second side panels, the back panel comprising a flexible substrate;
   a plurality of electrical connectors in electrical communication with the electrical stimulator and releasably attached to the substrate;
   a plurality of electrodes releasably connected to the plurality of electrical connectors;
   a plurality of locators releasably connected to the substrate to indicate a placement of the plurality of electrical connectors, wherein the plurality of locators each includes a layer of a hook and loop fastener for releasably attaching each of the plurality of locators to the substrate;
   wherein:
      the back panel is configured to extend across the lower back of the patient; and
      the first and second side panels are configured to be detachable and reattachable to respective first and second ends of the back panel, extend toward a front of the patient, and be fastened together to encircle, together with the back panel, a trunk of the patient at a level of the lumbar spine;
   and
   whereby, electrical stimulation is applied to the lower back by the electrical stimulator through the placement of the plurality of electrical connectors in contact with the plurality of electrodes to a prescribed area of the lower back as identified by the plurality of locators.

2. The electrical stimulation garment of claim 1 wherein the plurality of electrical connectors each includes a magnet.

3. The electrical stimulation garment of claim 2 wherein the plurality of electrodes each includes a magnet.

4. The electrical stimulation garment of claim 1 wherein the plurality of electrical connectors each includes a layer of a hook and loop fastener for releasably attaching each of the plurality of electrical connectors to the substrate.

5. The electrical stimulation garment of claim 4 wherein the plurality of electrodes each includes a layer of a hook and loop fastener for releasably attaching each of the plurality of electrodes to the substrate.

6. The electrical stimulation garment of claim 1 further comprising a plurality of lead wires for electrically interconnecting the plurality of electrical connectors with the electrical stimulator.

7. The electrical stimulation garment of claim 6 further comprising a plurality of channels for housing the plurality of lead wires.

8. The electrical stimulation garment of claim 7 wherein each of the plurality of channels is defined by an elongated flexible material attached to the substrate.

9. The electrical stimulation garment of claim 1, wherein each of the plurality of locators has a diameter smaller than an outer diameter of each of the plurality of electrical connectors.

10. The electrical stimulation garment of claim 1, further comprising a plurality of electrode icons, each detachable and reattachable to an inside surface of the flexible substrate, wherein each of the electrode icons helps a user to orient one of the plurality of electrodes relative to one of the plurality of electrical connectors.

11. An electrical stimulation garment comprising:
    an electrical stimulator configured to generate an electrical current sufficient to cause muscle contraction in a lower back of a patient;
    a back panel, a first side panel, and a second side panel, each made of stretchable and flexible material, wherein:
       the back panel includes a flexible substrate and is configured to extend across the lower back of the patient, and
       the first and second side panels are configured to be detachable and reattachable to respective first and second ends of the back panel, extend toward a front of the patient, and be fastened together to encircle, together with the back panel, a trunk of the patient at a level of the lumbar spine;
    a plurality of electrical connectors in electrical communication with the electrical stimulator and configured to be detachable and reattachable to the back panel of the substrate;
    a plurality of electrodes releasably connected to the plurality of electrical connectors; and
    a plurality of locators releasably connected to the back panel of the substrate to indicate a placement of the plurality of electrical connectors;
    whereby, electrical stimulation is applied to the lower back by the electrical stimulator through the placement of the plurality of electrical connectors in contact with the plurality of electrodes to a prescribed area of the lower back as identified by the plurality of locators.

12. The electrical stimulation garment comprising of claim 11, wherein each of the back panel, the first side panel and the second side panel are selectable from a variety of sizes and lengths and are interchangeable to fit the patient.

13. The electrical stimulation garment of claim 11, wherein the first side panel and second side panel are configured to pivot on the back panel to fit the patient.

14. The electrical stimulation garment of claim 11, further comprising a plurality of electrode icons, each detachable and reattachable to an inside surface of the flexible substrate, wherein each of the electrode icons helps a user to orient one of the plurality of electrodes relative to one of the plurality of electrical connectors.

* * * * *